United States Patent
Michelet

(10) Patent No.: US 10,835,468 B2
(45) Date of Patent: Nov. 17, 2020

(54) PARTICULAR PYRIDINEDICARBOXYLIC ACID DERIVATIVE/ANTIOXIDANT COMBINATION

(71) Applicant: L'OREAL, Paris (FR)

(72) Inventor: Francois Michelet, Creteil (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/537,628

(22) PCT Filed: Dec. 21, 2015

(86) PCT No.: PCT/EP2015/080830
§ 371 (c)(1),
(2) Date: Jun. 19, 2017

(87) PCT Pub. No.: WO2016/102489
PCT Pub. Date: Jun. 30, 2016

(65) Prior Publication Data
US 2018/0000712 A1    Jan. 4, 2018

(30) Foreign Application Priority Data
Dec. 22, 2014    (FR) ..................... 14 63104

(51) Int. Cl.
| | |
|---|---|
| A61K 8/49 | (2006.01) |
| A61Q 7/00 | (2006.01) |
| A61K 8/67 | (2006.01) |
| A61K 8/34 | (2006.01) |
| A61K 8/37 | (2006.01) |
| A61K 8/60 | (2006.01) |

(52) U.S. Cl.
CPC ............ *A61K 8/4926* (2013.01); *A61K 8/347* (2013.01); *A61K 8/37* (2013.01); *A61K 8/498* (2013.01); *A61K 8/4953* (2013.01); *A61K 8/602* (2013.01); *A61K 8/676* (2013.01); *A61Q 7/00* (2013.01)

(58) Field of Classification Search
None
See application file for complete search history.

(56) References Cited

U.S. PATENT DOCUMENTS

| | | |
|---|---|---|
| 4,717,727 A | 1/1988 | Gunzler et al. |
| 4,927,627 A | 5/1990 | Schrader et al. |
| 5,219,847 A | 6/1993 | Taguchi et al. |
| 5,472,617 A | 12/1995 | Barthold et al. |
| 5,472,687 A | 12/1995 | Proctor |
| 5,582,817 A | 12/1996 | Otsu et al. |
| 5,696,313 A | 12/1997 | Hafele |
| 5,786,379 A | 7/1998 | Bernardon |
| 5,945,441 A | 8/1999 | Steiner et al. |
| 6,020,139 A | 2/2000 | Schwartz et al. |
| 6,150,405 A * | 11/2000 | Proctor ............... A61K 8/46 514/474 |
| 6,399,613 B1 | 6/2002 | Bashiardes et al. |
| 7,598,278 B2 * | 10/2009 | Dalko .................. A61K 8/4926 424/59 |
| 8,431,653 B2 | 4/2013 | Ogawa et al. |
| 2003/0223945 A1 * | 12/2003 | Dalko .................. A61K 8/4926 424/70.1 |
| 2009/0215837 A1 | 8/2009 | Dalko et al. |
| 2010/0105741 A1 | 4/2010 | Dalko et al. |
| 2013/0131095 A1 | 5/2013 | Dalko et al. |

FOREIGN PATENT DOCUMENTS

| | | |
|---|---|---|
| CA | 2082076 A1 | 5/1993 |
| DE | 1242748 A1 | 3/2004 |
| EP | 0176741 A1 | 4/1986 |
| EP | 0433457 A1 | 6/1991 |
| EP | 0583479 A1 | 2/1994 |
| EP | 1352629 A1 | 10/2003 |
| ES | 2354103 * | 3/2011 |
| ES | 2354103 A1 | 3/2011 |
| FR | 2159400 A1 | 6/1973 |
| FR | 2677247 A1 | 12/1992 |
| FR | 2733053 A1 | 10/1996 |
| GB | 1354446 A | 6/1974 |
| GB | 1408036 A | 10/1975 |
| JP | 01-301612 A | 12/1989 |
| JP | 03-287536 A | 12/1991 |
| JP | H09-221442 A | 8/1997 |
| JP | H11-506426 A | 6/1999 |
| JP | 2001-253808 A | 9/2001 |
| JP | 2001-288048 A | 10/2001 |
| JP | 2002-080327 A | 3/2002 |
| JP | 2002-510302 A | 4/2002 |
| JP | 48-58149 B2 | 1/2012 |
| JP | 61-60655 B2 | 7/2017 |
| WO | 92/21317 A1 | 12/1992 |
| WO | 93/14749 A1 | 8/1993 |
| WO | 98/55091 A1 | 12/1998 |
| WO | 99/62483 A1 | 12/1999 |
| WO | 99/62881 A1 | 12/1999 |

OTHER PUBLICATIONS

Park et al. in Biomedical Research 31(1), 27-34 (2010) (Abstract) (Year: 2010).*

(Continued)

*Primary Examiner* — Dennis Heyer
(74) *Attorney, Agent, or Firm* — The Marbury Law Group, PLLC

(57) ABSTRACT

The invention relates to a cosmetic composition comprising one or more pyridinedicarboxylic acid derivatives of general formula (I) or a salt thereof and one or more antioxidants chosen from flavone heterosides, polyhydroxylated stilbenes, pyrimidinecarboxylic acid derivatives and ascorbic acid esters.

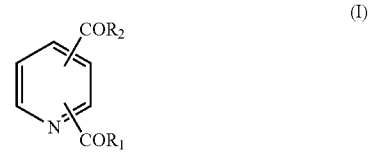

(I)

8 Claims, No Drawings

(56) References Cited

OTHER PUBLICATIONS

Juchaux et al. in International Journal of Cosmetic Science, 42, 167-173 (2020) (Year: 2020).*
International Search Report for PCT/EP2015/080830, dated Feb. 24, 2016.
Mintel: "Serum Jeunesse Hair Youth Serum," XP002744385, May 2015.
Shin, Seung Hyun et al., "Baicalin, a flavonoid, affects the activity of human dermal papilla cells and promotes anagen induction in mice," Naunyn-Schmiedebert's Archives of Pharmacology, vol. 388, No. 5, Dec. 2, 2014, pp. 583-586.

* cited by examiner

PARTICULAR PYRIDINEDICARBOXYLIC ACID DERIVATIVE/ANTIOXIDANT COMBINATION

CROSS REFERENCE TO RELATED APPLICATIONS

This is a national stage application of PCT/EP2015/080830, filed internationally on Dec. 21, 2015, which claims priority to French Application No. 1463104, filed on Dec. 22, 2014, both of which are incorporated by reference herein in their entireties.

The present invention relates to a cosmetic composition comprising at least one particular pyridinedicarboxylic acid derivative, or a salt thereof, and at least one antioxidant chosen from flavone heterosides, polyhydroxylated stilbenes, pyrimidinecarboxylic acid derivatives and ascorbic acid esters, and also to the use thereof for inducing and/or stimulating the growth of human keratin fibres such as the hair and the eyelashes and/or for curbing their loss.

The invention also relates to a cosmetic process for treating human keratin fibres using said composition.

The growth of the hair and its renewal are mainly determined by the activity of the hair follicles and their matrix environment. Their activity is cyclical and essentially comprises three phases, namely the anagenic phase, the catagenic phase and the telogenic phase.

The anagenic phase (active or growth phase), which lasts several years and during which the hairs lengthen, is followed by a very short and transient catagenic phase which lasts a few weeks, and then by a telogenic phase or resting phase which lasts a few months. At the end of the resting period, the hairs fall out and another cycle begins again. The head of hair is thus undergoing constant renewal and, of the approximately 150 000 hairs which make up a head of hair, approximately 10% are at rest and will be replaced in the months to come. The natural loss of the hair can be estimated, on average, at a few hundred hairs per day for a normal physiological state. This constant physical renewal process undergoes a natural change during the course of ageing; the hairs become finer and their cycles shorter. In addition, various causes may bring about substantial temporary or definitive hair loss. Hair loss, in particular alopecia, is essentially due to disruptions in hair renewal. These disruptions lead in a first stage to acceleration of the frequency of the cycles at the expense of the quality of the hairs, and then of their quantity. Progressive miniaturization of the bulbs takes place, in conjunction with isolation of these bulbs by gradual thickening of the perifollicular collagen matrix and also of the outer connective sheath. Revascularization around the hair follicle is thus made more difficult cycle after cycle. The hairs regress and become miniaturized until they are no more than an unpigmented down, and this phenomenon leads to gradual thinning of the head of hair. The number and mean diameter of the hair follicles that constitute the head of hair are affected. Certain areas are preferentially affected, especially the temporal or frontal lobes in men, and diffuse alopecia of the crown is observed in women.

The term "alopecia" also covers an entire family of hair follicle complaints whose final consequence is partial or general definitive hair loss. It may more particularly be a case of androgenic alopecia. In a large number of cases, early hair loss occurs in genetically predisposed individuals, which is known as andro-chrono-genetic alopecia; this form of alopecia especially concerns men. It is moreover known that certain factors, such as hormonal imbalance, physiological stress or malnutrition, can accentuate the phenomenon. In addition, loss or impairment of the hair can be in connection with seasonal phenomena.

Loss of hair density and hair loss are often experienced as distressing by persons thereby affected, especially when they are still young.

Pharmacological active agents such as minoxidil, latanoprost, fluridil, spironolactone and combinations thereof are known. However, they do not make it possible to maintain totally satisfactory hair density and may have adverse side effects.

Other products belonging to the cosmetic field exist. Among these, examples that may be mentioned include Aminexil® and Stemoxydine®.

However, consumers are still in search of more efficient products that have no adverse side effects, which would delay the process of "loss of hair density" or "excessive hair loss".

The Applicant has found, surprisingly and advantageously, that the combination of at least one pyridinedicarboxylic acid derivative of formula (I) as described below, or a salt thereof, with at least one antioxidant chosen from flavone heterosides, polyhydroxylated stilbenes, pyrimidinecarboxylic acid derivatives and ascorbic acid esters produces improved hypoxia-mimicking effects when compared with such a derivative of formula (I) alone or its combination with vitamin C.

This derivative is especially described in European patent application No. 1 352 629. An example of this derivative is sold under the trade name Stemoxydine® by the company L'Oreal.

Advantageously, the combination of the invention makes it possible to obtain improved effects on the head of hair especially regarding the hair density, the diameter or any other parameter that improves the quality of the head of hair, when compared with the use of stemoxydine alone.

One subject of the invention is thus a cosmetic composition comprising:
one or more pyridinedicarboxylic acid derivatives of general formula (I) or a salt thereof:

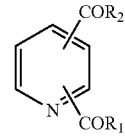

in which $R_1$ and $R_2$ represent, independently of each other, OH, OR', —$NH_2$, —NHR' or —NR'R", and
R' and R" represent, independently of each other, a linear or branched, saturated or unsaturated $C_1$-$C_{18}$ alkyl group, or an aryl group, this alkyl or aryl group being optionally substituted with one or more OH, alkoxy, acyloxy, amino or alkylamino groups, or R' and R" together represent a heterocycle, and
one or more antioxidants chosen from flavone heterosides, polyhydroxylated stilbenes, pyrimidinecarboxylic acid derivatives and ascorbic acid esters.

The present invention also relates to a cosmetic process for treating human keratin fibres and/or the scalp, comprising the application of the composition according to the invention to said fibres such as the hair and the eyelashes, and/or the scalp.

A subject of the invention is also the use of the cosmetic composition, for inducing and/or stimulating the growth of human keratin fibres such as the hair and the eyelashes, and/or for curbing their loss, and in particular for treating androgenic alopecia.

Other subjects, characteristics, aspects and advantages of the invention will emerge even more clearly on reading the description and the example that follows.

In the text hereinbelow, and unless otherwise indicated, the limits of a range of values are included within that range, especially in the expressions "between" and "ranging from . . . to . . . ". Moreover, the expression "at least one" used in the present description is equivalent to the expression "one or more".

According to the invention, the cosmetic composition comprises:
one or more pyridinedicarboxylic acid derivatives of general formula (I) or a salt thereof:

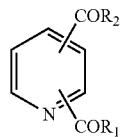

as defined above, and
one or more antioxidants chosen from flavone heterosides, polyhydroxylated stilbenes, pyrimidinecarboxylic acid derivatives and ascorbic acid esters.

The $C_1$-$C_{18}$ alkyl group is preferably a saturated or unsaturated alkyl group comprising from 1 to 10 carbon atoms, such as methyl, ethyl, tert-butyl, isopropyl or hexyl. The alkyl group may contain at least one carbon-carbon double bond or carbon-carbon triple bond, for instance —CH=$CH_2$, —$CH_2$—CH=CH—$CH_3$ or —$CH_2$—C≡CH.

According to the present invention, the term "alkoxy" means a group —O—R in which R is a $C_1$-$C_{18}$ alkyl group as defined previously.

The term "acyloxy" means a group —O—CO—R in which R is a $C_1$-$C_{18}$ alkyl group as defined previously.

The term "alkylamino" means a group —NH—R in which R is a $C_1$-$C_{18}$ alkyl group as defined previously.

The aryl group may represent the phenyl or naphthyl group.

When R' and R" together represent a heterocycle, they may represent a ring of 4 to 7 atoms and better still of 5 to 6 atoms, comprising from 1 to 4 heteroatoms chosen from O, S and N, this ring possibly being saturated or unsaturated. Heterocycles that may be mentioned include piperidine, morpholine, imidazole, pyrazole, piperazine, pyrrolidine and thiazolidine.

In particular, R' and R" represent a $C_1$-$C_{18}$ and better still $C_1$-$C_{10}$ alkyl group optionally substituted with an alkoxy or acyloxy group.

In formula (I), $R_1$ and $R_2$ preferably represent, independently of each other, —OH, —$OCH_3$, —O—$CH_2$—$CH_3$, —O—CH($CH_3$)$_2$, —O—$CH_2$—O—$COCH_3$, —NH—$CH_2$—$CH_2$—$CH_3$, —NH—$CH_2$—$CH_2OH$, —NH—$CH_2$—$CH_2$—$CH_2OH$ and —NH—$CH_2$—$CH_2OCH_3$.

In one particular embodiment, —$COR_1$ and —$COR_2$ are, respectively, in positions 2 and 3, or 2 and 4, of the pyridine nucleus. However, they may be in positions 2 and 5.

According to the invention, the term "salts of the derivative of formula (I)" means the mineral or organic salts of a derivative of formula (I).

As mineral salts that may be used according to the invention, mention may be made of the sodium or potassium double salts and also the zinc ($Zn^{2+}$), calcium ($Ca^{2+}$), copper ($Cu^{2+}$), iron ($Fe^{2+}$), strontium ($Sr^{2+}$), magnesium ($Mg^{2+}$) or manganese ($Mn^{2+}$) salts; hydroxides, carbonates and chlorides.

The organic salts that may be used according to the invention are, for example, the triethanolamine, monoethanolamine, diethanolamine, hexadecylamine, N,N,N',N'-tetrakis(2-hydroxypropyl)ethylenediamine and tris(hydroxymethyl)aminomethane salts.

Unless otherwise mentioned in the present description, the use of the expression "pyridinedicarboxylic acid derivative" includes the derivative in salified or non-salified form.

Examples of pyridinedicarboxylic acid derivatives that may especially be mentioned include:
2,4-pyridinedicarboxylic acid or the zinc or sodium salt thereof,
2,3-pyridinedicarboxylic acid or the zinc or sodium salt thereof,
dimethyl 2,4-pyridinedicarboxylate,
dimethyl 2,3-pyridinedicarboxylate,
diethyl 2,4-pyridinedicarboxylate,
diethyl 2,3-pyridinedicarboxylate,
diisopropyl 2,4-pyridinedicarboxylate,
2,4-bis(n-propylamido)pyridine (derivative of formula (I) with $R_1$ and $R_2$ representing —NH—($CH_2$)$_2$—$CH_3$),
di(acetyloxymethyl) 2,4-pyridinedicarboxylate (derivative of formula (I) with $R_1$ and $R_2$ representing —O—$CH_2$—O—$COCH_3$),
diethyl 2,5-pyridinedicarboxylate,
dimethyl 2,5-pyridinedicarboxylate,
2,4-bis(2-hydroxyethylamido)pyridine, and
2,4-bis(3-hydroxypropylamido)pyridine.

Advantageously, the pyridinedicarboxylic acid derivative is in pyridinedicarboxylic acid ester form. The particularly preferred derivative is diethyl 2,4-pyridinedicarboxylate. It is sold, for example, under the trade name Stemoxydine® by the company L'Oreal.

The derivative(s) or a salt thereof are present in an amount preferably ranging from $10^{-3}$% to 10% by weight, better still from 0.1% to 8% by weight and even more preferentially from 0.5% to 5% by weight, relative to the total weight of the composition.

The oxidizing agent(s) used in the composition according to the present invention are chosen from flavone heterosides, polyhydroxylated stilbenes, pyrimidinecarboxylic acid derivatives and ascorbic acid esters.

Examples of flavone heterosides that may especially be mentioned include baicalin, apigetrin, rhofolin, vitexin, tetuin and apiin.

Examples of polyhydroxylated stilbenes that may especially be mentioned include resveratrol or else pinosylvin.

An example of a pyrimidinecarboxylic acid derivative that may especially be mentioned is ectoin.

Examples of ascorbic acid esters that may especially be mentioned include ascorbyl palmitate, ascorbyl linoleate, ascorbyl oleate and magnesium 2-ascorbyl phosphate.

Preferably, the antioxidants(s) are chosen from baicalin, resveratrol, ectoin and ascorbyl palmitate, and mixtures thereof.

The antioxidants(s) are present in an amount preferably ranging from 0.1% to 15% by weight, even better still from 0.5% to 10% by weight and even more preferentially from 0.7% to 6% by weight, relative to the total weight of the composition.

The composition according to the invention is preferably aqueous and then comprises water at a concentration preferably ranging from 5% to 98% by weight, especially from 20% to 95% by weight and better still from 50% to 95% by weight, relative to the total weight of the composition.

The composition may also comprise one or more organic solvents that are liquid at 25° C. and 1.013×10$^5$ Pa and which are especially water-soluble, such as $C_1$-$C_7$ alcohols, especially $C_1$-$C_7$ aliphatic or aromatic monoalcohols, and $C_3$-$C_7$ polyols and polyol ethers, which may thus be used alone or as a mixture with water. Advantageously, the organic solvent may be chosen from ethanol, isopropanol and propylene glycol, and mixtures thereof.

The composition of the invention is preferably a composition intended for cosmetic use in topical application to the skin and keratin fibres, and more especially to the scalp, the hair and the eyelashes.

According to the application method, this composition may be in any galenical form normally used in cosmetics, such as a lotion, serum, milk, O/W or W/O cream, gel, ointment, pomade, powder, balm, patch, impregnated pad, soap, bar or foam.

For topical application to the skin, including the scalp, the composition may especially be in the form of an aqueous, alcoholic or aqueous-alcoholic solution or suspension, an oily suspension or solution, an emulsion or dispersion of liquid or semi-liquid consistency obtained by dispersing a fatty phase in an aqueous phase (O/W) or vice versa (W/O), a dispersion or emulsion of soft consistency, an aqueous or aqueous-alcoholic or oily (anhydrous) gel, a loose or compact powder to be used as is or to be incorporated into a physiologically acceptable medium (excipient), or alternatively microcapsules or microparticles, or vesicular dispersions of ionic and/or nonionic type.

It is also possible to envisage a composition in the form of a foam or alternatively in the form of an aerosol composition also comprising a pressurized propellant.

In particular, the composition for application to the scalp or the hair may be in the form of a haircare lotion, for example for daily or twice-weekly application, a shampoo or a hair conditioner, in particular for twice-weekly or weekly application, a liquid or solid soap for cleansing the scalp for daily application, a hairstyle shaping product (lacquer, hair-setting product, styling gel), a treatment mask, a cream or a foaming gel for cleansing the hair. It may also be in the form of a hair dye or a hair mascara to be applied by brush or comb.

According to a particular embodiment, the composition is in the form of a hair cream or lotion, a shampoo, a hair conditioner, a hair mascara or a mascara for the eyelashes.

The composition according to the invention may also contain adjuvants that are common in cosmetics, which are conventionally used in an amount ranging from 0.01% to 20% and better still from 0.1% to 10% of the total weight of the composition.

The present invention also relates to a cosmetic process for treating human keratin fibres and/or the scalp, comprising the application of a composition according to the invention to the fibres and/or the scalp, and more particularly the hair, the eyelashes and/or the scalp.

In particular, the process comprises the steps of applying a composition according to the invention to the scalp and/or the fibres, and optional rinsing. In the case of rinsing, the leave-on time of the composition may range from 1 minute to 30 minutes.

Preferably, the cosmetic composition according to the invention is not rinsed off.

The examples that follow serve to illustrate the invention.

EXAMPLES

The following protocol was followed: the tests were performed on human keratinocytes in culture, seeded on Greiner brand 48-well plates, coated with bovine collagen I.

The plates were prepared according to the following procedure: the solution of bovine collagen I at 0.1 mg/ml was prepared by dilution in phosphate-buffered saline (PBS) of the bovine collagen I solution sold by the company Life Technologies. Each well was immersed with 1 ml of this dilution, which was left at the bottom of the wells for 1 hour at 37° C. At the end of the incubation, the collagen solution was removed and the wells were rinsed twice with 1 ml of PBS. The plates were then stored at 4° C. until the time of use.

The tests are performed using primary human keratinocytes at a rate of 23 800 cells/cm$^2$ of wells coated with bovine collagen I as explained previously, followed by culturing for 72 hours in the presence of 500 µl of KGM medium sold by the company Lonza, supplemented with:
- 0.1% by weight of gentamicin sulfate/amphotericin mixture sold under the commercial brand GA-1000 by the company Lonza (CC-3101/CC-4131),
- 0.4% by weight of bovine pituitary gland extract sold under the commercial brand BPE by the company Lonza,
- 0.1% by weight of insulin sold under the commercial brand insulin by the company Lonza,
- 0.1% by weight of hydrocortisone and
- 0.1% by weight of epidermal growth factor (or recombinant human EGF sold under the commercial brand Epidermal growth factor by the company Lonza), at 37° C. under an atmosphere saturated with water and containing 5% $CO_2$.

The cells were then treated with the various compounds (stemoxydine, vitamin C, resveratrol, baicalin, ectoin, ascorbyl palmitate and mixtures thereof with stemoxydine) in concentrations ranging up to the highest non-cytotoxic concentration, for 72 hours under normoxia (21% oxygen).

Following this culturing and treatment, the cell lawns were washed with phosphate-buffered saline (or PBS) and then lysed using a lysis buffer proposed in the kit from the supplier Qiagen. The RNAs were then extracted using the RNeasy isolation kit and the Qiacube robotic workstation, both sold by the company Qiagen, according to the manufacturer's instructions.

The quantity and quality of RNAs were controlled using the LabChip® GX bioanalyser from Perkin-Elmer before performing reverse transcription (RT) using the Qiagen kit and according to the supplier's recommendations (Quanti-Tect reverse transcription kit). The cDNA obtained following the RT was then amplified by real-time quantitative PCR using a specific kit sold under the commercial brand Light-Cycler® 480 SYBR Green Master Mix by the company Roche (Cat. No. 14123920) and an LC480 thermocycler (Roche). The PCRs were performed in triplicate (n=3). The information relating to the primers used is presented below.

Priming was performed using specific standard primers sold by the company Qiagen, the references for which are BNIP3/QT00024178/Hs_BNIP3-1-SG Quantitect Assay Primer; CA9/QT00011697/Hs_CA9-1-SG Quantitect Assay Primer; EGNL3/QT00025900/Hs_EGNL3-1-SG Quantitect Assay Primer; RPL13A/QT00089915/Hs_RPL13A-1-SG Quantitect Assay Primer, and the fluorescent probe of brand name SYBR Green sold by the company specified previously.

The PCR was performed in three phases:
- denaturing phase for 10 minutes at 95° C.,
- amplification phase which consists of 45 cycles comprising:
  - a step of denaturing for 30 seconds at 95° C.,
  - a step of hybridization for 30 seconds at 60° C., and
  - a step of elongation at 72° C. for 30 seconds,
- melting phase for ensuring the quality of the hybridizations.

The incorporation of SYBR Green into the amplified DNA was measured continuously during the amplification cycles. These measurements make it possible to obtain curves of fluorescence intensity as a function of the PCR cycles and thus to evaluate the relative expression of each marker from the cycle thresholds (Ct), corresponding to the number of cycles required to appropriately detect a fluorescence level. For each marker and for each condition, the relative expression (RE) value was normalized relative to the expression of the reference gene RPL13.

The expression of each gene is normalized by that of the "stable referent gene" (or "housekeeping gene" RPL13A, ribosomal gene). The results ("fold change" (Fc)) are expressed relative to the control.

The genes used are hypoxia-sensitive (HIF-1 alpha signalling pathway) and are collated in Table 1 below.

TABLE 1

| Name | Abbreviation | Accession number | Function |
|---|---|---|---|
| Carbonic anhydrase IX | CA9 | NM_001216 | Regulation of the intracellular pH |
| BCL2/adenovirus E1B 19 kDa-interacting protein | BNIP3 | NM_004052 | Control of the cell apoptosis |
| Prolyl hydroxylase | EGLN3 (or Egg-laying nine homolog 3, or PHD3) | NM_022073 | Hydroxylation of collagen and HIF-1alpha |
| Ribosomal protein L13 | RPL13 | NM_000977 | Referent gene |

Three hypoxia-sensitive genes (BNIP3, EGLN3 and CA9) were used in the following examples. Three tests were performed according to the protocol described above for each gene and for each compound or combination. The results are expressed as a function of the expression of the referent gene RPL13 (control) (1.00) and indicated in the tables below, the mean and the standard deviation being indicated in parentheses.

Example 1 (Comparative): Effect of Stemoxydine Alone or Combined with Vitamin C on the Expression of a Selection of Genes in Relation with the Described Effects of Hypoxia

TABLE 2

| Gene | Vitamin C 100 μM | Vitamin C 10 μM | Stemoxydine 300 μM | Control |
|---|---|---|---|---|
| BNIP3 | 0.98/1.32/1.07 (1.12 ± 0.18) | 1.02/1.13/0.89 (1.01 ± 0.12) | 1.51/1.65/2.13 (1.76 ± 0.32) | 1 ± 0 |
| EGLN3 | 1.05/1.51/1.16 (1.24 ± 0.24) | 0.92/1.41/0.89 (1.07 ± 0.29) | 2.15/2.09/3.56 (2.60 ± 0.83) | 1 ± 0 |
| CA9 | 1.43/1.51/0.74 (1.22 ± 0.42) | 1.19/1.43/0.43 (1.02 ± 0.52) | 3.87/3.86/5.86 (4.53 ± 1.15) | 1 ± 0 |

| Gene | Vitamin C 100 μM + Stemoxydine 300 μM | Vitamin C 10 μM + Stemoxydine 300 μM |
|---|---|---|
| BNIP3 | 1.72/1.98/2.3 (2 ± 0.23) | 1.63/1.9/2 (1.84 ± 0.19) |
| EGLN3 | 3.01/3.35/4.33 (3.56 ± 0.68) | 2.15/2.64/2.43 (2.40 ± 0.24) |
| CA9 | 6.39/6.74/8.13 (7.09 ± 0.92) | 5.33/4.8/4.93 (5.02 ± 0.28) |

Example 2 (Invention): Effect of Stemoxydine Alone or Combined with Resveratrol on the Expression of a Selection of Genes in Relation with the Described Effects of Hypoxia

TABLE 3

| Genes | Resveratrol 1 μM | Resveratrol 0.3 μM | Stemoxydine 300 μM | Control |
|---|---|---|---|---|
| BNIP3 | 1.10/2.35/2.57 (2.01 ± 0.79) | 1.05/1.53/1.21 (1.26 ± 0.24) | 1.51/1.65/2.13 (1.76 ± 0.32) | 1 ± 0 |
| EGLN3 | 1.62/4.65/4.69 (3.65 ± 1.76) | 1.31/2.36/2.10 (1.92 ± 0.55) | 2.15/2.09/3.56 (2.60 ± 0.83) | 1 ± 0 |
| CA9 | 2.34/1.97/1.75 (2.02 ± 0.33) | 1.82/1.75/1.31 (1.63 ± 0.28) | 3.87/3.86/5.86 (4.53 ± 1.15) | 1 ± 0 |

| Genes | Resveratrol 1 μM + Stemoxydine 300 μM | Resveratrol 0.3 μM + Stemoxydine 300 μM |
|---|---|---|
| BNIP3 | 2.28/4.68/7.23 (4.73 ± 2.48) | 1.9/2.21/3.39 (2.5 ± 0.79) |
| EGLN3 | 5.04/13.13/13.18 (10.45 ± 4.69) | 4.68/5.46/11.53 (7.22 ± 3.75) |
| CA9 | 8.99/10.87/10.38 (10.08 ± 0.98) | 9.98/7.96/11 (9.65 ± 1.55) |

The results show a synergistic effect on the expression of the genes BNIP3, EGLN3 and CA9 when stemoxydine is combined with resveratrol. In addition, these effects are higher than those for the stemoxydine+vitamin C combination.

Example 3 (Invention): Effect of Stemoxydine Alone or Combined with Baicalin on the Expression of a Selection of Genes in Relation with the Described Effects of Hypoxia

TABLE 4

| Gene | Baicalin 30 μM | Baicalin 3 μM | Stemoxydine 300 μM | Control |
|---|---|---|---|---|
| BNIP3 | 1.14/1.41/1.15 (1.23 ± 0.15) | 0.99/1.27/1.06 (1.11 ± 0.15) | 1.51/1.65/2.13 (1.76 ± 0.32) | 1 ± 0 |
| EGLN3 | 1.70/2.47/2.03 (2.07 ± 0.39) | 1.00/1.33/1.25 (1.19 ± 0.17) | 2.15/2.09/3.56 (2.60 ± 0.83) | 1 ± 0 |
| CA9 | 1.06/1.07/0.6 (0.91 ± 0.27) | 1.27/1.18/0.74 (1.06 ± 0.28) | 3.87/3.86/5.86 (4.53 ± 1.15) | 1 ± 0 |

| Gene | Baicalin 30 μM + Stemoxydine 300 μM | Baicalin 3 μM + Stemoxydine 300 μM |
|---|---|---|
| BNIP3 | 2.10/2.19/2.07 (2.12 ± 0.06) | 2.10/1.99/2.77 (2.29 ± 0.42) |
| EGLN3 | 5.94/8.65/5.87 (6.82 ± 1.59) | 4.61/3.88/6.21 (4.90 ± 1.19) |
| CA9 | 8.25/7.95/7.71 (7.97 ± 0.27) | 8.89/6.75/9.23 (8.29 ± 1.34) |

The results show a synergistic effect on the expression of the genes BNIP3, EGLN3 and CA9 when stemoxydine is combined with baicalin. In addition, these effects are higher than those for the stemoxydine+vitamin C combination.

Example 4 (Invention): Effect of Stemoxydine Alone or Combined with Ascorbyl Palmitate on the Expression of a Selection of Genes in Relation with the Described Effects of Hypoxia

TABLE 5

| Gene | Ascorbyl palmitate 30 µM | Ascorbyl palmitate 10 µM | Stemoxydine 300 µM | Control |
|---|---|---|---|---|
| BNIP3 | 1.04/1.6/0.81 (1.15 ± 0.41) | 1.01/1.35/0.95 (1.10 ± 0.22) | 1.51/1.65/2.13 (1.76 ± 0.32) | 1 ± 0 |
| EGLN3 | 1.02/2.04/0.43 (1.16 ± 0.81) | 1.4/1.78/0.87 (1.35 ± 0.46) | 2.15/2.09/3.56 (2.60 ± 0.83) | 1 ± 0 |
| CA9 | 1.09/1.73/0.14 (0.99 ± 0.80) | 1.65/2.00/1.25 (1.63 ± 0.38) | 3.87/3.86/5.86 (4.53 ± 1.15) | 1 ± 0 |

| Gene | Ascorbyl palmitate 30 µM + Stemoxydine 300 µM | Ascorbyl palmitate 10 µM + Stemoxydine 300 µM |
|---|---|---|
| BNIP3 | 2.21/2.51/2.34 (2.35 ± 0.15) | 2.42/2.25/2.50 (2.39 ± 0.13) |
| EGLN3 | 4.05/3.93/3.50 (3.83 ± 0.29) | 5.42/3.77/4.82 (4.67 ± 0.84) |
| CA9 | 8.23/8.21/6.56 (7.67 ± 0.96) | 9.42/8.36/11.14 (9.64 ± 1.40) |

The results show a synergistic effect on the expression of the genes BNIP3, EGLN3 and CA9 when stemoxydine is combined with vitamin C palmitate. These effects are higher in all respects than those for the stemoxydine+vitamin C combination.

Example 5 (Invention): Effect of Stemoxydine Alone or Combined with Ectoin on the Expression of a Selection of Genes in Relation with the Described Effects of Hypoxia

TABLE 6

| Gene | Ectoin 300 µM | Ectoin 100 µM | Stemoxydine 300 µM | Control |
|---|---|---|---|---|
| BNIP3 | 1.40/1.79/1.66 (1.62 ± 0.2) | 1.31/1.77/1.77 (1.62 ± 0.27) | 1.51/1.65/2.13 (1.76 ± 0.32) | 1 ± 0 |
| EGLN3 | 2.07/2.82/2.97 (2.62 ± 0.48) | 2.48/2.76/3.46 (2.90 ± 0.50) | 2.15/2.09/3.56 (2.60 ± 0.83) | 1 ± 0 |
| CA9 | 2.23/2.54/2.93 (2.57 ± 0.35) | 2.73/2.55/3.74 (3.01 ± 0.64) | 3.87/3.86/5.86 (4.53 ± 1.15) | 1 ± 0 |

| Gene | Ectoin 300 µM + Stemoxydine 300 µM | Ectoin 100 µM + Stemoxydine 300 µM |
|---|---|---|
| BNIP3 | 2.30/2.56/2.98 (2.61 ± 0.34) | 2.20/2.37/2.65 (2.41 ± 0.23) |
| EGLN3 | 3.88/3.51/4.01 (3.80 ± 0.26) | 5.03/3.56/4.18 (4.25 ± 0.74) |
| CA9 | 6.86/5.86/7.27 (6.66 ± 0.73) | 8.38/5.87/7.56 (7.27 ± 1.28) |

The results show a synergistic effect on the expression of the genes BNIP3, EGLN3 and CA9 when stemoxydine is combined with ectoin.

The compositions of the invention may be used, for example, as a lotion applied at a rate of 1 ml of lotion to the scalp, at a frequency of one to two times per day. The compositions described below may also be thickened using a thickening polymer.

Example 6: Example of Lotion

| | |
|---|---|
| Diethyl 2,4-pyridinedicarboxylate | 0.5 g to 5 g |
| Resveratrol | 0.2 g |
| Propylene glycol | 10.0 g |
| Isopropyl alcohol | qs 100.0 g |

Example 7: Example of Lotion

| | |
|---|---|
| Diethyl 2,4-pyridinedicarboxylate | 0.5 g to 5 g |
| Ascorbyl palmitate | 2 g |
| Propylene glycol | 10.0 g |
| Isopropyl alcohol | qs 100.0 g |

The invention claimed is:

1. A cosmetic composition comprising:
   one pyridinedicarboxylic acid derivative which is diethyl 2,4-pyridinedicarboxylate,
   and
   one antioxidant which is resveratrol.

2. The cosmetic composition according to claim 1, wherein the pyridinedicarboxylic acid derivative is present in an amount ranging from $10^{-3}$% to 10% by weight, relative to the total weight; of the composition.

3. The cosmetic composition according to claim 1, wherein the antioxidant is present in an amount ranging from 0.1% to 15% by weight, relative to the total weight of the composition.

4. The cosmetic composition according to claim 1, wherein the pyridinedicarboxylic acid derivative is present in an amount ranging from 0.5% to 5% by weight relative to the total weight of the composition.

5. The cosmetic composition according to claim 1, wherein the antioxidant is present in an amount ranging from 0.7% to 6% by weight relative to the total weight of the composition.

6. A cosmetic process for treating human keratin fibres and/or the scalp, comprising the application to said fibres and/or the scalp of a composition comprising:
   one pyridinedicarboxylic acid derivative which is diethyl2,4-pyridinedicarboxylate,
   and
   one antioxidant which is resveratrol.

7. A method for inducing and/or stimulating the growth of human keratin fibres, and/or for curbing their loss, the method comprising applying a composition comprising:
   one pyridinedicarboxylic acid derivative which is diethyl2,4-pyridinedicarboxylate,
   and
   one antioxidant which is resveratrol.

8. The method according to claim 7, for treating androgenic alopecia.

* * * * *